United States Patent [19]

Clausen

[11] 4,274,558
[45] Jun. 23, 1981

[54] DISPENSING OF FLUENT MATERIALS

[76] Inventor: Anthony R. Clausen, 7 Klip St., Observatory, Johannesburg, Transvaal Province, South Africa

[21] Appl. No.: 922,270

[22] Filed: Jul. 6, 1978

[30] Foreign Application Priority Data

Jul. 7, 1977 [ZA] South Africa .................... 77/4095

[51] Int. Cl.³ .............................................. B65D 37/00
[52] U.S. Cl. ..................................... 222/214; 222/309; 417/476; 128/215; 222/333; 128/223
[58] Field of Search ................ 222/206, 209, 214, 309, 222/291, 372, 333; 417/474–477; 128/DIG. 1, DIG. 12, 218 A, 216, 215, 222–223

[56] References Cited

U.S. PATENT DOCUMENTS

| | | | |
|---|---|---|---|
| 2,696,173 | 12/1954 | Jensen | 417/477 |
| 2,898,859 | 8/1959 | Corneil | |
| 3,386,630 | 6/1968 | Haviland | 222/309 |
| 3,786,683 | 1/1974 | Berman | 417/476 |
| 3,807,131 | 4/1974 | Samson | 417/476 |
| 3,930,761 | 1/1976 | Barraclough | 417/476 |
| 4,138,205 | 2/1979 | Wallach | 417/477 |

Primary Examiner—H. Grant Skaggs
Attorney, Agent, or Firm—Donal B. Tobin

[57] ABSTRACT

A dispensing device for use in dispensing measured quantities of fluent material through a resiliently compressible dispensing tube, the device comprising a housing having a tube zone for receiving a dispensing tube, collapsing apparatus adapted to be rotatably driven by drive apparatus relatively to a tube located in the tube zone to collapse the tube in a compression zone and to advance the compression zone along a compression arc to dispense fluent material through the tube, and adjustment apparatus for adjusting the effective length of the compression arc, the adjustment apparatus comprising an adjustable cam member to co-operate with the collapsing apparatus and control the effective length of a compression arc during a revolution of the collapsing apparatus.

8 Claims, 5 Drawing Figures

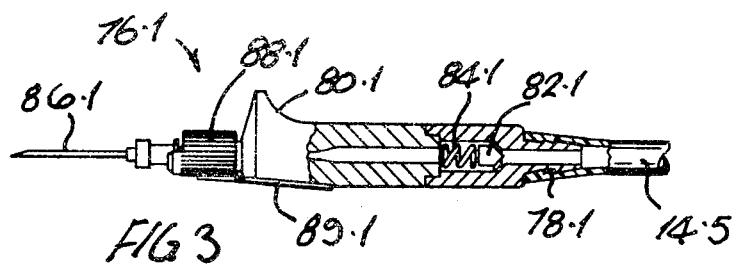
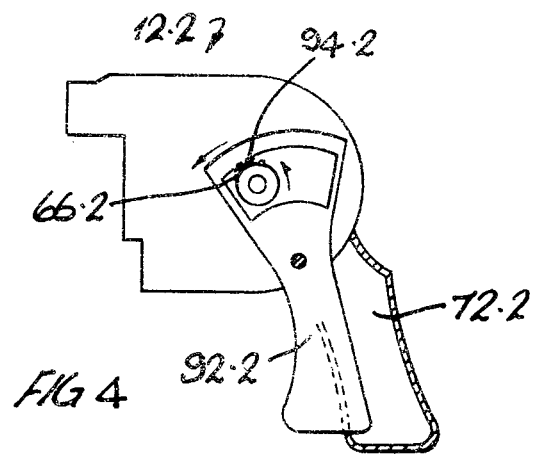
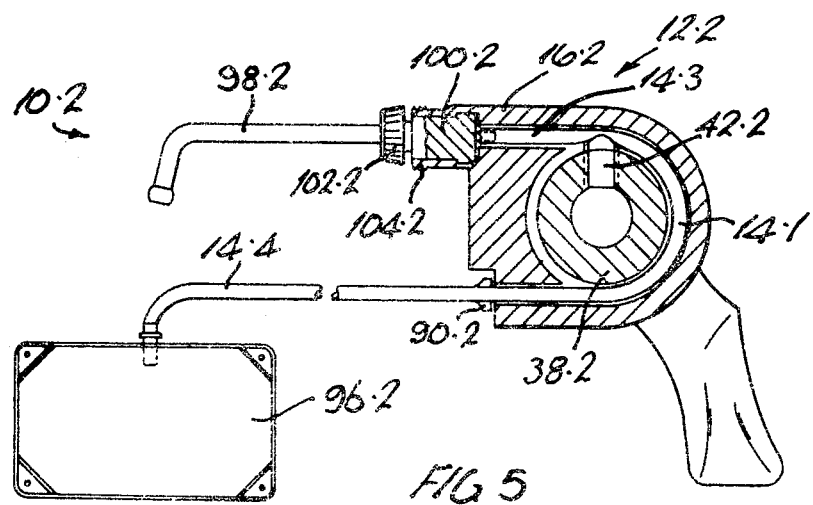

DISPENSING OF FLUENT MATERIALS

THIS INVENTION relates to the dispensing of fluent materials. More particularly, this invention relates to a dispensing device for use in dispensing fluent materials and to a dispensing kit for use in dispensing fluent materials.

According to the invention there is provided a dispensing device for use in dispensing measured quantities of fluent material through a resiliently compressible dispensing tube, the device comprising a housing having a tube zone for receiving a dispensing tube, collapsing means adapted to be rotatably driven relatively to a tube located in the tube zone to collapse the tube in a compression zone and to advance the compression zone along a compression arc to dispense fluent material through the tube, and adjustment means for adjusting the effective length of the compression arc.

In an embodiment of the invention, the adjustment means may comprise an adjustable cam member to co-operate with the collapsing means and control the effective length of a compression arc during a revolution of the collapsing means.

In one example of this embodiment of the invention, the adjustable cam member may be adapted to co-operate with the collapsing means to cause the collapsing means to be rotated eccentrically relatively to a tube located in the tube zone, with the adjustable cam member being adjustable to adjust the eccentric movement of the collapsing means and thus the effective length of a compression arc during a revolution of the collapsing means.

In an alternative example of this embodiment of the invention, the collapsing means may include a radially displaceable compression member which is slidably mounted on the collapsing means, and the cam member may be adapted to co-operate with the compression member to control the effective length of a compression arc effected by the compression member.

The compression member may include bias means operative between it and the cam member to allow for manufacturing tolerances in the wall thicknesses of a dispensing tube being used in the dispensing device, to combat the compression member becoming jammed against a collapsed dispensing tube if the wall thicknesses of the tube are slightly oversize, and to combat the compression member failing to collapse the tube completely if the wall thicknesses of such a tube are slightly undersize.

In an alternative embodiment of the invention, the adjustment means may comprise means to adjust the effective length of a tube presented to the collapsing means in the tube zone.

Thus, for example, the tube zone may have a curved compression surface against which the tube is compressed by the collapsing means during use, with the compression surface having one or more removable panels to allow the effective length of the compression surface to be altered and thus the effective length of a tube presented to the collapsing means in the tube zone.

The dispensing device of this invention may be adapted to have drive means mounted thereof for rotatably driving the collapsing means.

In an alternative embodiment of the invention, the dispensing device may include drive means mounted thereon for rotatably driving the collapsing means.

The dispensing device may further include control means for controlling operation of the drive means, the control means being adjustable to allow the collapsing means to be rotatably driven through a selected angle upon each actuation of the drive means.

Thus, for example, the control means may be adjustable to allow the collapsing means to be rotatably driven through a selected angle of less than 180 degrees, through a selected angle of less than 360 degrees, or through a selected angle of more than 360 degrees upon each actuation of the drive means.

In one embodiment of the invention, the drive means may comprise a displaceable lever member.

The lever member may be in the form of a manually displaceable lever member, in the form of a foot operated lever member, or the like.

In this embodiment of the invention, the control means may be adapted to control the extent by which the displaceable lever can be displaced upon actuation thereof, thereby controlling the angle through which the collapsing means is rotatably driven upon actuation of the lever member.

In an alternative embodiment of the invention, the drive means may comprise an electric motor adapted for connection to a suitable power source.

In this embodiment of the invention, the control means may be operatively associated with the electric motor to control pivotal displacement of the electric motor upon actuation thereof, and thus the angle through which the collapsing means is rotatably driven upon actuation of the electric motor.

The electric motor may be adapted for connection to any suitable power source such as the mains outlet, a vehicle battery, a rechargeable battery mounted on the dispensing device, or the like.

In an embodiment of the invention, the dispensing device may have a dispensing tube outlet zone, with mounting means at the outlet zone for mounting a dispensing nozzle on the outlet zone.

The dispensing nozzle may be in the form of an oral dosing nozzle of conventional type for oral administration of a veterinary remedy. Alternatively, for dispensing a spot-on remedy, the dispensing nozzle may be in the form of a spot-on dispensing nozzle of any conventional type.

The dispensing device of this invention may have any suitable securing means for securing a dispensing tube in position in the tube zone to restrain axial displacement of a tube located in the tube zone during use.

In an embodiment of the invention, the securing means may be provided by a closure plate which is mounted on the tube zone after a dispensing tube has been located therein, and engages frictionally with the dispensing tube.

In an alternative embodiment of the invention, the dispensing device may have a dispensing tube inlet zone leading to the tube zone, with the inlet zone having securing means for co-operating with a dispensing tube to combat axial displacement of a tube located in the tube zone during use.

The invention further extends to a dispensing kit comprising a dispensing device as described herein, and a resiliently compressible dispensing tube for location in the tube zone.

The dispensing tube may conveniently be of a resiliently compressible synthetic plastics material.

The dispensing tube may conveniently be of elliptical cross-section to facilitate collapsing of the dispensing tube by the collapsing means during use.

By having the dispensing tube of elliptical cross section, it will be appreciated that by varying the length of the major axis of the tube, the volume of fluent material dispensed by the dispensing device during use, can effectively by varied.

Thus, depending upon the dosage range of fluent material to be dispensed for each fluent material, the cross sectional area of a dispensing tube may be selected or formed accordingly.

The dispensing tube may conveniently be connected to a collapsible fluent material container. It may conveniently be integrally connected to the fluent material container.

The fluent material container may contain a fluent material to be dispensed, so that the fluent material is housed in the container in a sterile condition when the dispensing tube is sealed by any suitable means, prior to use.

The dispensing tube and fluent material container containing the fluent material, can thus be supplied in a sterile sealed condition.

In an embodiment of the invention, where the fluent material is in the form of an injectable solution or an injectable slurry, a needle or a floating needle may be operatively mounted at the free end of the dispensing tube.

In an embodiment of the invention, the floating needle may be integrally mounted on the tube, for disposal with the tube and fluent material container after use.

The needle may conveniently be in the form of a floating needle for use at a point remote from the dispensing device.

In this embodiment of the invention, the floating needle may conveniently incorporate a one way valve to combat reverse flow, with the one way valve being biassed to combat dripping under the action of gravity when the device is not in use.

In an alternative embodiment of the invention, the dispensing tube may be provided with a dispensing nozzle mounted at its free end.

In an embodiment of the invention, the dispensing tube may have a shoulder formation to co-operate with the dispensing device during use, to combat axial displacement of the tube under the action of the collapsing means.

The dispensing device may, in one embodiment of the invention, be in the form of a gun with a handle portion to allow it to be held by hand.

In an alternative embodiment of the invention, the dispensing device may be in the form of a dispensing unit to be placed at a suitable location or to be suspended on the body of an operator.

This invention may have application wherever measured doses of fluent material are to be dispensed from time to time or in short succession.

Thus, for example, the invention can have particular application for dispensing veterinary remedies, pesticides, toxic substances, medicines, dosing materials, and the like.

Embodiments of the invention are now described by way of example with reference to the accompanying drawings.

In the drawings:

FIG. 3 shows, to an enlarged scale, a fragmentary, partly sectional plan view of a floating dispensing member attached to a dispensing tube of the dispensing kit of this invention, and having a needle mounted thereon;

FIG. 4 shows a diagrammatic, fragmentary, partly sectional side elevation of an alternative embodiment of a dispensing device in accordance with this invention; and FIG. 5 shows a diagrammatic, fragmentary, partly sectional side elevation of the dispensing device of FIG. 4, forming part of a dispensing kit in accordance with this invention.

Figure 1:
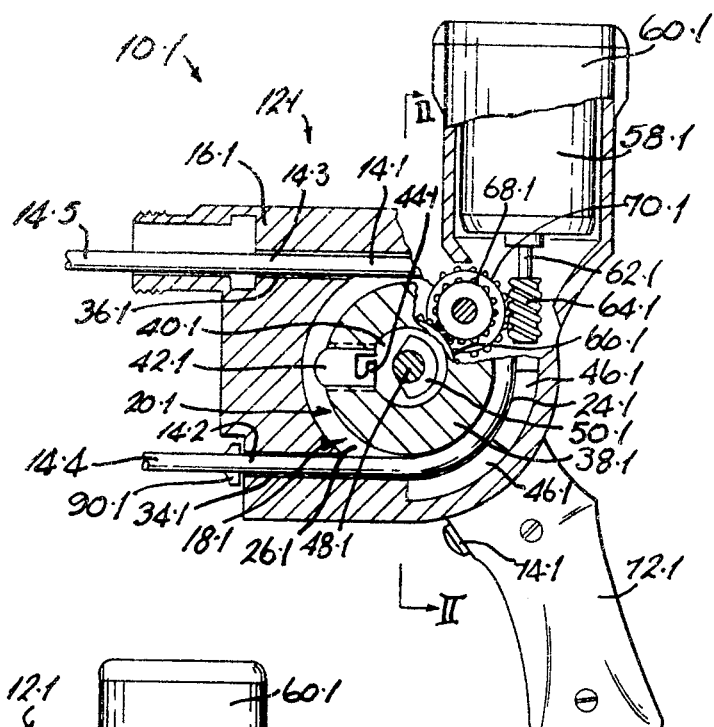
FIG. 1 shows a diagrammatic, fragmentary, partly sectional side elevation along line I—I of FIG. 2, of one embodiment of a dispensing kit in accordance with this invention.
Figure 2:
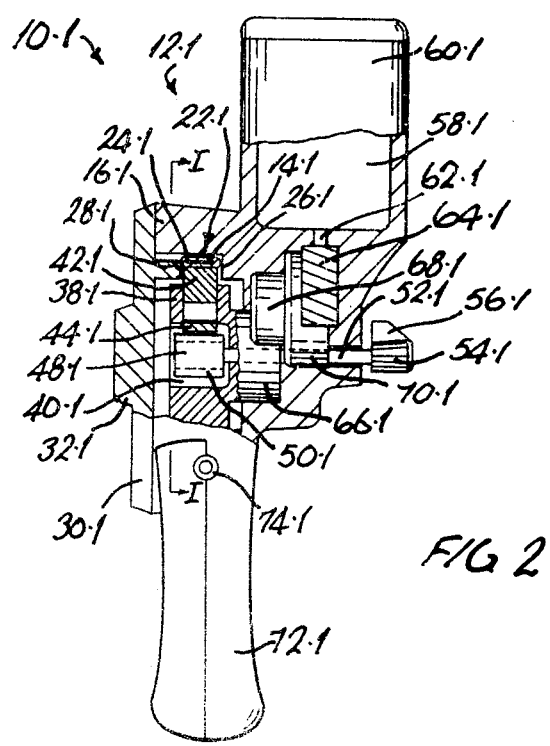
FIG. 2 shows a diagrammatic, fragmentary, partly sectional front elevation along line II—II of FIG. 1, of the dispensing kit of this invention, with the compression member of the collapsing means trailing its position as shown in FIG. 1 by 90 degrees.

With reference to FIGS. 1 to 3 of the drawings, reference numeral 10.1 refers generally to a dispensing kit for use in dispensing predetermined quantities of an injectable veterinary remedy from a collapsible veterinary remedy container (not shown).

The dispensing kit 10.1 comprises a dispensing device 12.1 having a dispensing tube 14.1 operatively located therein.

The dispensing device 12.1 comprises a housing 16.1 having a tube zone 18.1 wherein the dispensing tube 14.1 is firmly located.

The dispensing device 12.1 further comprises collapsing means 20.1 which is adapted to be rotatably driven relatively to the tube 14.1 to collapse the tube 14.1 in a compression zone 22.1 (as shown in FIG. 2) and to advance the compression zone along a compression arc to dispense the veterinary remedy through the tube 14.1

The tube zone 18.1 is defined by a semi-circular compression wall 24.1 against which the tube 14.1 is compressed by the collapsing means 20.1 during use.

The tube zone 18.1 is further defined by a base wall 26.1 and by an opposed semi-annular flange 28.1 which depends from a cover plate 30.1 having a knob 32.1 (as shown in FIG. 2).

The cover plate 30.1 is removable from the housing 16.1 to expose the tube zone 18.1. After the dispensing tube 14.1 has been located in position in the tube zone 18.1, the cover plate can be fixed to the housing 16.1 to close the tube zone and, at the same time, to allow the semi-annular flange 28.1 to locate the tube 14.1 between it and the base wall 26.1.

The housing 16.1 further has an inlet groove 34.1 wherein an inlet portion 14.2 of the tube 14.1 is located, and an outlet groove 36.1 wherein an outlet portion 14.3 of the dispensing tube 14.1 is located.

The flange 28.1 of the cover plate 30.1 is further shaped to co-operate with the inlet and outlet grooves 34.1 and 36.1 to locate the tube 14.1 in position in the dispensing device 12.1.

The collapsing means 20.1 comprises a rotary member 38.1 having a hollow bore 40.1.

The rotary member 38.1 has a radially displaceable compression member 42.1 slidably mounted thereon for radial displacement relatively to the rotary member 38.1.

The compression member 42.1 has opposed flanges along its opposed sides which are slidably receivable in corresponding slots in the rotary member 38.1 to allow the compression member 42.1 to be slidably displaced in the radial direction.

The compression member 42.1 is formed with a resilient portion 44.1 which is resiliently flexible to serve the purpose as will be hereinafter described.

The dispensing device 12.1 further includes adjustment means for adjusting the effective length of the compression arc during a revolution of the rotary member 38.1.

Two alternative forms of adjustment means are shown in the dispensing device 12.1. It will be appreciated however, that either of these forms may be employed alone, if desired.

The first form of adjustment means for adjusting the effective length of a compression arc during use, is provided by the compression wall 24.1 being defined by curved panels 46.1 which are removably located within the housing 16.1.

Each curved panel 46.1 extends through an arc of 45 degrees and is independently removable.

It will be appreciated that where a curved panel 46.1 has been removed, the collapsing means 20.1 will not collapse the tube 14.1 in that zone as the compression member traverses the portion of the tube 14.1 in that zone, and thus the effective length of the tube presented to the collapsing means is reduced and the effective length of the compression arc is reduced accordingly.

It will be appreciated that in this embodiment of the invention, where the means for adjusting the effective length of the compression arc resides in the curved panels 46.1 only, the compression member may be fixed to the rotary member 38.1 or may be omitted entirely. Where it is omitted entirely, the rotary member 38.1 will be provided with a suitable compression projection corresponding to that provided by the compression member 42.1.

The alternative form of adjustment means for adjusting the effective length of the compression arc comprises an adjustable cam member 48.1 having a camming surface 50.1 which extends through an angle of 180 degrees.

The cam member 48.1 with its camming surface 50.1 is located within the hollow bore 40.1, and has an adjustment shaft 52.1 extending therefrom through a suitable bore in the housing 16.1.

The adjustment shaft 52.1 terminates in an adjustment knob 54.1 having a pointer 56.1 mounted thereon.

In use, if the rotary member 38.1 is rotatably driven with the cam member 48.1 in the position indicated in FIGS. 1 and 2 of the drawings, the compression member 42.1 will co-operate with the camming surface 50.1 so that the camming surface 50.1 will force the compression member 42.1 against the tube 14.1 to collapse the tube 14.1 in a compression zone vertically below the central axis of the cam member 48.1 when the rotary member 38.1 is rotated in an anti-clockwise direction as shown in FIG. 1 of the drawings. Thereafter, the compression zone will be advanced by the compression member 42.1 through an arc of 180 degrees until the compression member 42.1 reaches the position vertically above the axis of the cam member 48.1 as shown in FIG. 2 of the drawings.

However, if the adjustable cam member 48.1 is pivotally displaced through an angle of 90 degrees from the position illustrated in the drawings, and located in such new position, the cam will only be effective in forcing the compression member 42.1 against the tube 14.1 to collapse the tube, through an arc of 90 degrees.

Thus the quantity of fluent material dispensed during such a rotation of the rotary member 38.1 will be half the quantity previously dispensed when the compression arc extended through an angle of 180 degrees.

In this way, by adjusting the position of the adjustable cam member 48.1 by means of the adjustable knob 54.1, the quantity of fluent material dispensed on each revolution of the rotary member 38.1 can be varied as required.

Markings relating to different masses of animals to be treated with a particular veterinary remedy may be marked on the outside of the dispensing device 12.1 so that by means of the pointer 56.1, the adjustment knob 54.1 can be adjusted for an appropriate quantity of fluent material to be dispensed per revolution in relation to the estimated mass of an animal being treated.

It will be noted that the camming surface 50.1 co-operates with the resilient portion 44.1 to displace the compression member 42.1 radially outwardly during use.

The resilient portion 44.1 therefore allows for manufacturing tolerances in the wall thicknesses of the dispensing tube 14.1 to combat the compression member 42.1 becoming jammed between the collapsed tube and the compression wall 24.1 if the wall thicknesses of the tube 14.1 are slightly oversize, and to combat failure to collapse the tube 14.1 entirely if the wall thicknesses thereof are slightly undersized.

The dispensing device 12.1 includes drive means for rotatably driving the rotary member 38.1.

In the embodiment illustrated in FIGS. 1 to 3 of the drawings, the drive means comprises an electric motor 58.1 mounted in a motor housing 60.1 extending upwardly from the housing 16.1.

The electric motor has a drive shaft 62.1 extending therefrom, with the drive shaft having a gear 64.1 mounted thereon.

The rotary member 38.1 has an annular section from which an annular gear or bearing section 66.1 extends thereon below the hollow bore 40.1.

The annular gear 66.1 has a bore through which the adjustment shaft 52.1 slidably extends.

The annular gear 66.1 and the gear 64.1 are operatively connected by means of a gear train 68.1 and 70.1.

The electric motor 58.1 is adapted for connection to a suitable power source.

The dispensing device 12.1 includes control means (not shown) of any conventional type for controlling operation of the electric motor 58.1 to allow the electric motor 58.1 to rotatably drive the rotary member 38.1 through a selected angle upon each actuation of the electric motor 58.1.

The control means may therefore be adjusted so that upon each actuation of the electric motor 58.1, the rotary member 38.1 is rotatably driven through any angle less than 180 degrees, less than 360 degrees, or through an angle greater than 360 degrees.

Thus, by suitably setting the control means, the dispensing kit 10.1 can be operated so that a desired quantity of fluent material can be dispensed upon each actuation of the motor 58.1.

Thus, for example, it can be set so that the rotary member 38.1 executes a single revolution upon each actuation of the motor 58.1, or a plurality of revolutions, depending upon the quantity of fluent material to be dispensed on each occasion.

The dispensing device 12.1 includes a handle 72.1 by which it may be held for use.

A finger control button 74.1 is provided on the handle 72.1 for actuating the electric motor 58.1.

The dispensing tube 14.1 is formed out of a resiliently compressible synthetic plastics material and is of a convenient length for effective use.

The dispensing tube 14.1 has its trailing end 14.4 integrally connected to a collapsible fluent material container containing the veterinary remedy to be dispensed. It has its leading end 14.5 connected to a dispensing member 76.1 in the form of a floating dispensing member as shown in FIG. 3 of the drawings.

The dispensing member 76.1 is molded out of a suitable synthetic plastics material, and has a barbed spigot portion 78.1 for securing it to the leading end 14.5 of the tube 14.1.

To ensure hygienic use of the dispensing member 76.1, it may conveniently be integrally connected to the dispensing tube 14.1 to combat re-use thereof.

The dispensing member 76.1 is shaped to be conveniently held by hand, and has a thumb-receiving flange 80.1.

The dispensing member 76.1 has a valve closure member 82.1 located within its bore, to combat any reverse flow of fluent material through it.

The valve closure member 82.1 is lightly biassed by means of a spring 84.1 to combat dripping of fluent material out of the dispensing member 76.1 under the action of gravity when it is not in use.

The dispensing member 76.1 is shown having a conventional needle 86.1 mounted thereon by means of a conventional type of threaded cap 88.1.

If desired, a conventional frangible or tamperproof label 89.1 can be provided on the threaded cap 88.1 and the dispensing member 76.1 so that it will be broken when the threaded cap 88.1 is removed to unseal the dispensing member 76.1. It will thus be readily apparent if the member has been opened or tampered with and if there is therefore doubt as to whether or not the veterinary remedy is still in a hygienic and uncontaminated condition.

The dispensing member 76.1 is thus in the form of a so-called floating needle which can be gripped by hand and forced into a suitable location on an animal, whereafter it can be released while the veterinary remedy is dispensed through the dispensing tube 14.1 by the dispensing device 12.1 of this invention, and into the animal through the needle 86.1. After the required dose has been dispensed, the dispensing member 76.1 can be withdrawn and can then be applied to a further animal.

In use, prior to fitting of the needle 86.1, the dispensing member 76.1 will be sealed by the threaded cap 88.1.

Thus the assembly of the dispensing tube 14.1, the collapsible fluent material container (not shown) containing the veterinary remedy, and the dispensing member 76.1 will be maintained in a sealed hygienic condition where it cannot be contaminated.

This provides the advantage that the veterinary remedy can be stored and supplied in a hygienically sealed condition. When required for use, it can readily be fitted into the dispensing device 12.1 for dispensing the veterinary remedy.

This provides the further advantage that since the veterinary remedy does not come into contact with the dispensing device 12.1, it eliminates the need to sterilise the dispensing device 12.1 from time to time.

The compression member 42.1 is conveniently of a synthetic plastics material which is of the self-lubricating type thereby ensuring free rotation of the rotary member 38.1 and combatting frictional resistance between the compression member 42.1 and the dispensing tube 14.1 during use.

As can be seen in FIG. 1 of the drawings, the dispensing tube 14.1 has a shoulder formation 90.1 mounted thereon on the trailing side of its inlet portion 14.2.

The shoulder formation 90.1 abuts the housing 16.1 at the inlet of the inlet groove 34.1, thereby restraining the dispensing tube 14.1 against axial displacement with the rotary member 38.1 during use.

It is an advantage of the embodiment of the invention as illustrated in the drawings that once the veterinary remedy contained in the fluent material container has been used, the entire assembly of the dispensing member 76.1, the dispensing tube 14.1 and the fluent material container can be disposed of. In this way, the inadvertent use of a contaminated remedy will be avoided.

In addition, any wear that may occur on the dispensing tube 14.1 will be negligible because of the short time for which the tube is in use.

The embodiment of the invention as illustrated in the drawings provides the further advantage that even where the veterinary remedy is in the form of a slurry or the like, it will not subject the dispensing device 12.1 to undue wear.

The embodiment of the invention as illustrated in the drawings provides the further advantages that the dispensing tube 14.1 can readily be located in position in the dispensing device 12.1, and that the dispensing device 12.1 can be set by means of the adjustable cam member 48.1, by means of the removable panels 46.1 and/or by means of the control means to provide infinite variations in the dosages to be dispensed on each occasion during use.

By appropriately setting the dispensing device 12.1 a large variety of veterinary remedies can be effectively dispensed in desired dosages for various animals and various animals of different masses.

With reference to FIG. 4 of the drawings, reference numberal 12.2 refers generally to an alternative embodiment of a dispensing device to the dispensing device 12.1.

The dispensing device 12.2 corresponds substantially with the dispensing device 12.1 except that an alternative form of drive means is provided for rotatably driving the rotary member 38.1 (not shown in FIG. 4).

The drive means comprises a pivotally mounted lever 92.2.

The lever 92.2 is associated with the handle 72.2 for manual displacement.

The lever 92.2 has a gear portion 94.2 to cooperate with the annular gear 66.2 of the rotary member 38.1.

The dispensing device 12.2 includes a return spring (not shown) to displace the lever 92.2 back into its inoperative position. It further includes a suitable directional clutch or the like, to release the annular gear 66.2 from the gear portion 94.2 during return of the lever 92.2 to its inoperative position after it has been manually compressed into the handle 72.2 during use.

The lever 92.2 is such and its co-operation with the annular gear 66.2 is such that upon compression of the lever 92.2 into the handle 72.2, the rotary member will be rotatably driven through an angle of 360 degrees.

The dispensing device 12.2 further includes a stop member (not shown) provided in the handle 72.2 which can be actuated to limit the movement of the lever 92.2, and thus adjust the extent by which the rotary member is rotated upon actuation of the lever 92.2.

With reference to FIG. 5 of the drawings, reference numeral 10.2 refers generally to an alternative embodiment of a dispensing kit in accordance with this invention.

The dispensing kit 10.2 comprises a dispensing device 12.2 corresponding to the dispensing device of FIG. 4.

The lever 92.2 has been omitted for the sake of clarity, but the rotary member 38.2 and the compression member 42.2 have been shown.

The dispensing kit 10.2 is shown having the trailing end 14.4 of the dispensing tube 14.1 connected to a collapsible fluent material container 96.2 containing the veterinary remedy to be dispensed.

The dispensing kit 10.2 is shown having an oral dosing nozzle 98.2 of conventional type, operatively mounted on the dispensing device 12.2, with the outlet portion 14.3 of the dispensing tube 14.1, sealingly connected to the nozzle 98.2.

The nozzle is located in position by having a locating portion 100.2 located within a complementary bore in the housing 16.2, and by having a threaded cap 102.2 to co-operate with a threaded portion 104.2.

It will be appreciated that, if desired, a nozzle 98.2 may be mounted in the same way on the dispensing device 12.1.

It will be appreciated that corresponding parts of the dispensing device 12.2 as illustrated in FIGS. 4 and 5 of the drawings, which correspond with those parts of the dispensing device 12.1 have been indicated by corresponding reference numerals except that, where appropriate, the reference numeral has the suffix '.2' instead of the suffix '.1'.

I claim:

1. A dispensing device for use in dispensing measured quantities of fluent material through a resilient, compressible dispensing tube, the device comprising:
    a housing having a generally cylindrical recess therein, said recess having an open top and said recess having a base defined by a base wall, and said recess having a side defined by a peripheral wall extending from said base;
    a cover for said recess including a peripheral flange extending into said recess in confronting relationship to said base wall and spaced apart therefrom;
    a rotatable member having an annular section and a bearing section, said bearing section rollably engaging said housing and supporting said annular section for rotation in said recess;
    the circumferential portion of said annular section projecting into the space between the confronting surface of said cover flange and said base wall and spaced radially apart from the peripheral wall to define a compression zone;
    an inlet passage to said recess through said housing and said peripheral wall;
    an outlet from said recess through said housing and said peripheral wall;
    a compression member projecting from said annular section into said compression zone toward said housing peripheral wall; and,
    adjustment means to adjust the effective length of a tube presented to the compression member in said compression zone.

2. A dispensing device as claimed in claim 1 further including a resilient compressible dispensing tube for location in the tube zone.

3. A dispensing device according to claim 2, in which the dispensing tube is integrally connected to a collapsible fluent material container.

4. A dispensing device according to claim 3, in which the fluent material container contains a fluent material to be dispensed.

5. A dispensing device according to claim 2 further including a dispensing nozzle mounted at the free end of said dispensing tube.

6. A dispensing device according to claim 2 further including a shoulder formation to cooperate with the dispensing device to combat axial displacement of the tube during use.

7. The apparatus of claim 1 wherein said adjustment means includes an arcuate recess in at least a portion of said peripheral wall confronting said compressive zone; and,
    one or more arcuate panels removably disposed in said arcuate recess;
    whereby the removal of one or more of said arcuate panels widens the compression zone so that the compression member will not compress the tube in the tube zone and thereby the effective length of the tube is varied.

8. The apparatus of claim 1 wherein said annular section includes an aperture extending substantially radially through said annular section wall for receiving said compression member;
    cooperative means disposed in said aperture and on said compression member for holding said compression member in said aperture;
    and said adjustment means includes a cam member disposed within an open, central portion of said annular section and adapted to operatively engage a drive means;
    said cam member having a cam surface cooperatively engaging said compression member over a selectable portion of the rotation of said rotatable member.

* * * * *